United States Patent [19]
Rappoport et al.

[11] Patent Number: 5,509,936
[45] Date of Patent: Apr. 23, 1996

[54] DUAL LEAF SPRING STRUT SYSTEM

[76] Inventors: Albert F. Rappoport, P.O. Box 3256, Santa Monica, Calif. 90408; Jerome P. Voisin, 145 Agnes St., Houma, La. 70363

[21] Appl. No.: 268,336
[22] Filed: Jun. 30, 1994
[51] Int. Cl.[6] .......................................... A61F 2/60
[52] U.S. Cl. .................. 623/27; 623/38; 623/50; 623/52
[58] Field of Search .................................. 267/158, 164; 623/27, 38, 42, 50, 52; 135/65, 68, 72

[56] References Cited

U.S. PATENT DOCUMENTS

| | | | |
|---|---|---|---|
| 49,529 | 8/1865 | Jewett | 623/52 |
| 312,396 | 2/1885 | Spring | 623/50 |
| 875,482 | 3/1907 | Wyatt | 623/27 |
| 1,035,760 | 10/1911 | Walton | 135/72 |
| 2,241,481 | 8/1939 | Schroeder | 135/72 |
| 2,678,054 | 5/1954 | Bostelman | 623/38 |
| 4,547,913 | 10/1985 | Phillips | 623/27 |
| 4,718,913 | 1/1988 | Voisin | 623/49 |
| 4,822,363 | 4/1989 | Phillips | 623/27 |
| 5,019,109 | 5/1991 | Voisin | 623/49 |
| 5,165,125 | 11/1992 | Callaway | 267/164 |
| 5,217,500 | 6/1993 | Phillips | 623/38 |
| 5,341,829 | 8/1994 | Hsiao et al. | 135/72 |

FOREIGN PATENT DOCUMENTS

| | | | |
|---|---|---|---|
| 2032281 | 5/1980 | United Kingdom | 623/38 |
| 9410943 | 5/1994 | WIPO | 623/55 |

OTHER PUBLICATIONS

"Walking Members for Bilateral Amputation of Thigh" Apr. 1933, J. Bone & Joint Surg.

Primary Examiner—David H. Willse
Assistant Examiner—Bruce E. Snow
Attorney, Agent, or Firm—Pravel, Hewitt, Kimball & Krieger

[57] ABSTRACT

A lower leg prosthetic assembly having an anterior and posterior components, comprising curved linear leaf springs extending along substantially the length of the assembly, each spring bowed away from one another along substantially their mid-length. There is further provided a wedge member for engaging the lower end of each spring while in position in a prosthetic foot, and wedgingly securing the anterior and posterior springs to a prosthetic foot member, for allowing increased rotation at the ankle joint. Further the upper ends of the leaf springs may be secured to the upper portion of the assembly with a wedge member, wedgingly securing the springs to the upper member, or attached to a socket member, both types of attachments for decreasing rotation at the knee joint. There may be further provided an achilles strap extending along the posterior spring for offering additional vertical loading without increased elongation of the rear spring.

15 Claims, 5 Drawing Sheets

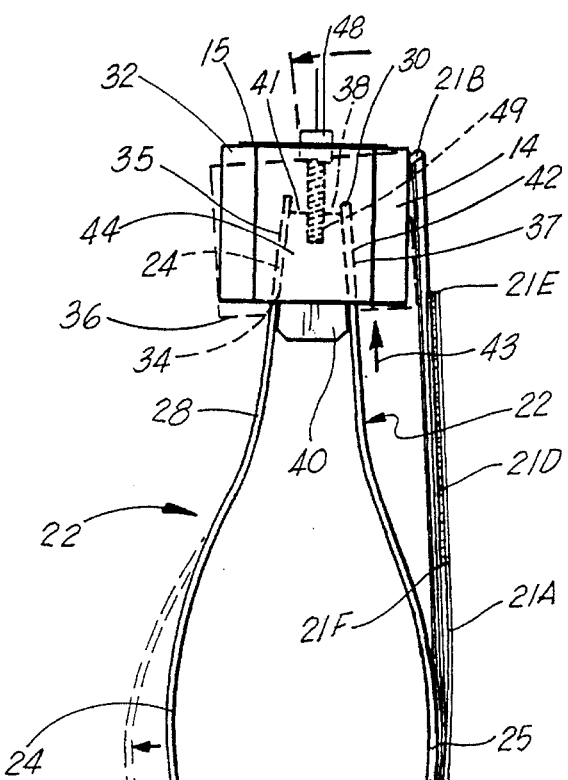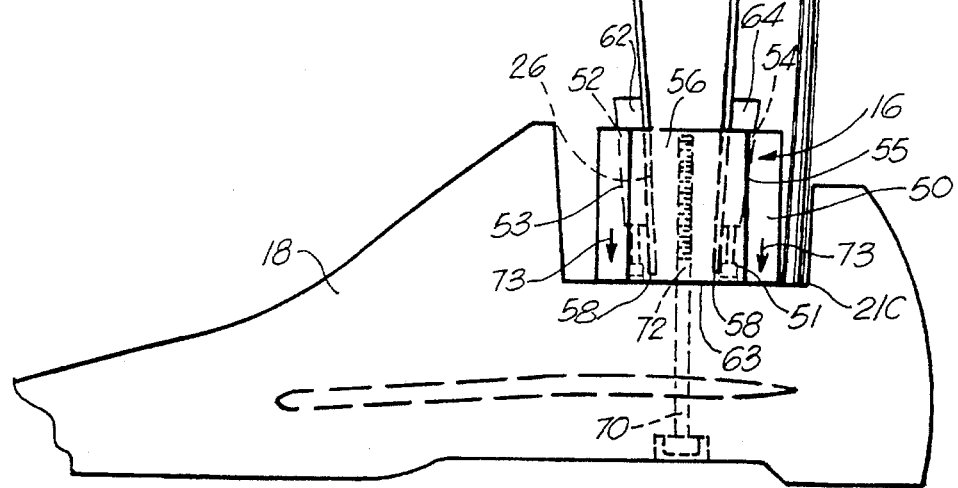
FIG. 2

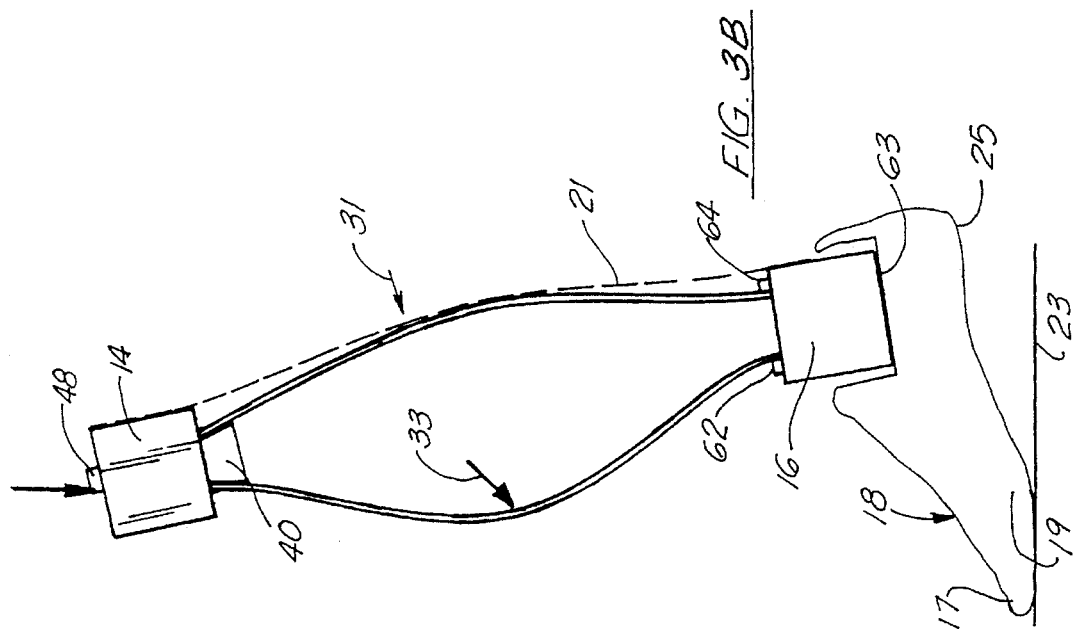
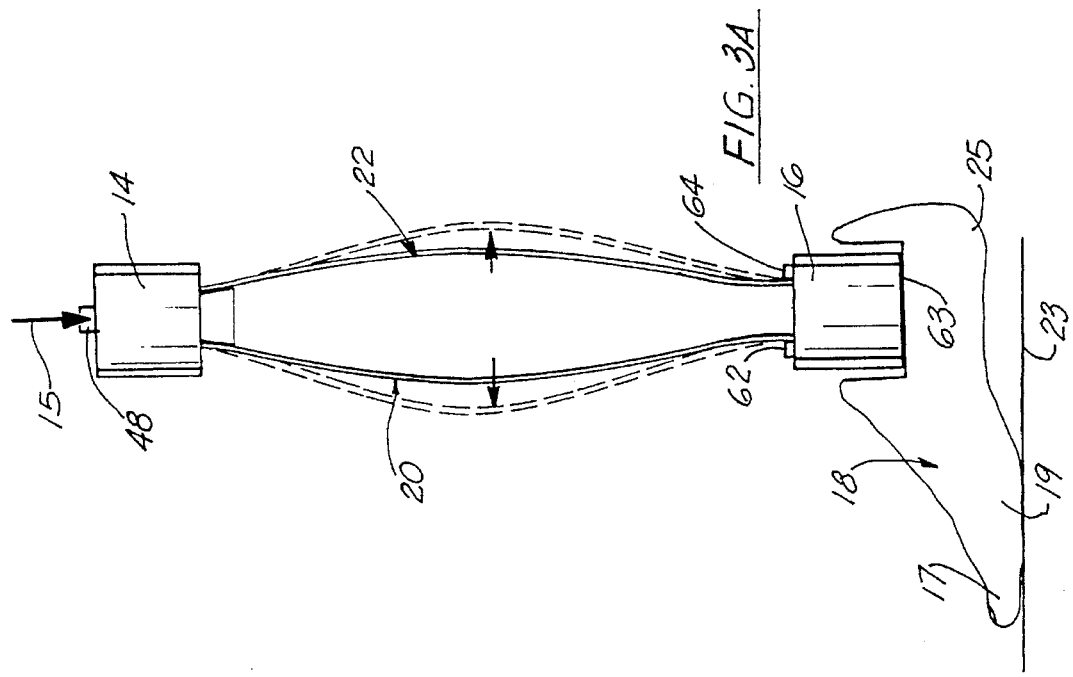

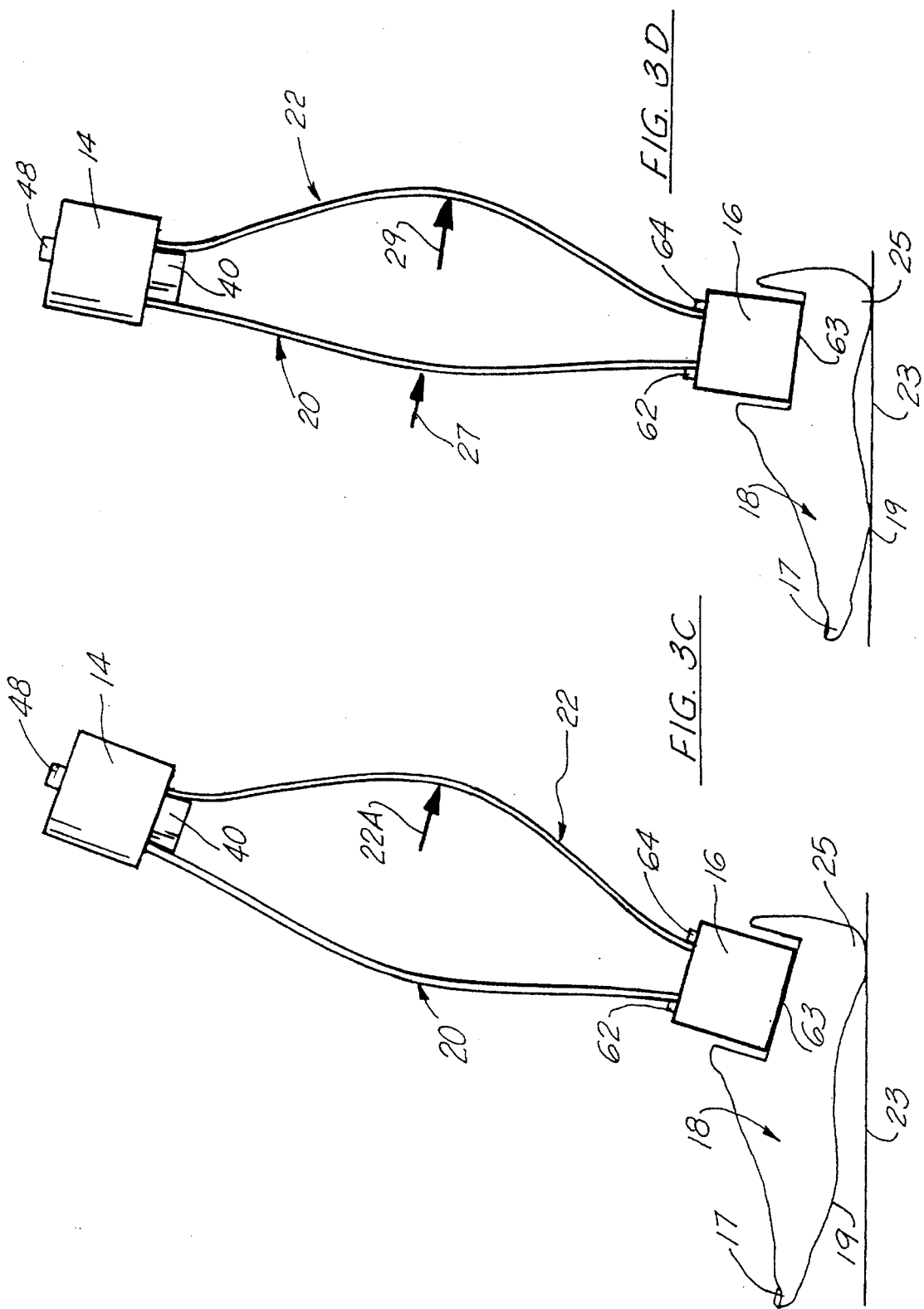

DUAL LEAF SPRING STRUT SYSTEM

BACKGROUND OF THE INVENTION

1. Field of the Invention

The present invention relates to prosthetic limbs. More particularly, the present invention relates to strut system positioned between the upper leg and a prosthetic foot of an amputee which provides for increased rotation at the ankle joint and reduced rotation at the knee joint.

2. General Background

One of the inventors has obtained patents on first, a dual, ankle, springs prosthetic foot and ankle system, issued under U.S. Pat. No. 4,718,913, utilizing a pair of helical springs secured to a top ankle plant and to a plantar base plate. Placement of this system into a substantially rigid artificial foot, allowed, to a certain degree, normal walking movement, with the compression and elongation of the two springs depending on the various points in a walking movement. Likewise, a second patent, entitled Multi-axial Rotation System For Artificial Ankle, issued under U.S. Pat. No. 5,019,109, utilized a pair of compressible members, positioned in parallel relation, and attached to upper and lower plates, the assembly secured within a rigid artificial foot. The compressible members may be pre-compressed to provide the stepping movement during walking, similar to the '913 patent.

In both of these systems, the upper portion of the assembly would be rigidly attached to a lower leg prothesis, in order to complete the prosthetic assembly. However, in order to provide more normal walking ability, the lower leg, or calf prothesis had to be addressed. In the art, there exists device, patented under U.S. Pat. No. 4,822,363, entitled "Modular Composite Prosthetic Foot and Leg," which provides a prosthesis fabricated from laminants having a pylon with an upper extremity, a shin portion, an ankle portion and a forwardly extending foot portion, and a heel portion secured to the assembly. A second patent, U.S. Pat. No. 4,547,913, entitled "Composite Prosthetic Foot and Leg" which also utilizes high-strength fibers and has a unitary construction.

The patents cited above are provided in applicant's Prior Art Statement, which is being submitted herewith.

SUMMARY OF THE PRESENT INVENTION

The improved strut system of the present invention solves problems in the art in a straightforward manner. What is provided is a lower leg prosthetic assembly having an anterior and posterior components, comprising curved linear leaf springs extending along substantially the length of the assembly, each spring bowed away from one another along substantially their mid-length. There is further provided wedge members for engaging the lower end of each spring while in position in a prosthetic foot, and wedgingly securing the anterior and posterior springs to a prosthetic foot member, for allowing increased rotation at the ankle joint. Further the upper ends of the leaf springs are secured to the upper portion of the assembly with a wedge member, wedgingly securing the springs to the upper member, for allowing decreased rotation at the knee joint or socket, in cases where the socket would be laminated directly to the spring members. There may be further provided an achilles strap extending along the posterior spring for offering additional vertical loading without increased tension (elongation) of the rear spring.

Therefore, it is a principal object of the present invention to provide a lower leg prosthetic device for generating flexion or bending moments during operation;

It is a further object of the present invention to provide and improved prosthetic strut system which utilizes a pair of curved linear leaf springs adapted to the upper knee portion (socket) and lower ankle portion through a bolting/wedging attachment for allowing greater rotation at the ankle and less rotation at the knee joint or socket;

It is still an object of the present invention to provide an improved prosthetic lower leg strut which combines a pair of linear leaf springs frictionally engaged to the prosthetic knee and prosthetic ankle of the wearer for receiving greater flexion or bending, and for achieving greater rotation of the ankle joint over current prosthetic devices.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 2 illustrates a side partial cutaway view of the the preferred embodiment of the prosthetic apparatus of the present invention, utilizing an achilles tendon portion;

FIGS. 3-A through 3-D illustrate plan elevational views of the prosthetic apparatus of the present invention as the foot is undergoing the motions involved in walking.

DETAILED DESCRIPTION OF THE PREFERRED EMBODIMENT

Figure 1:
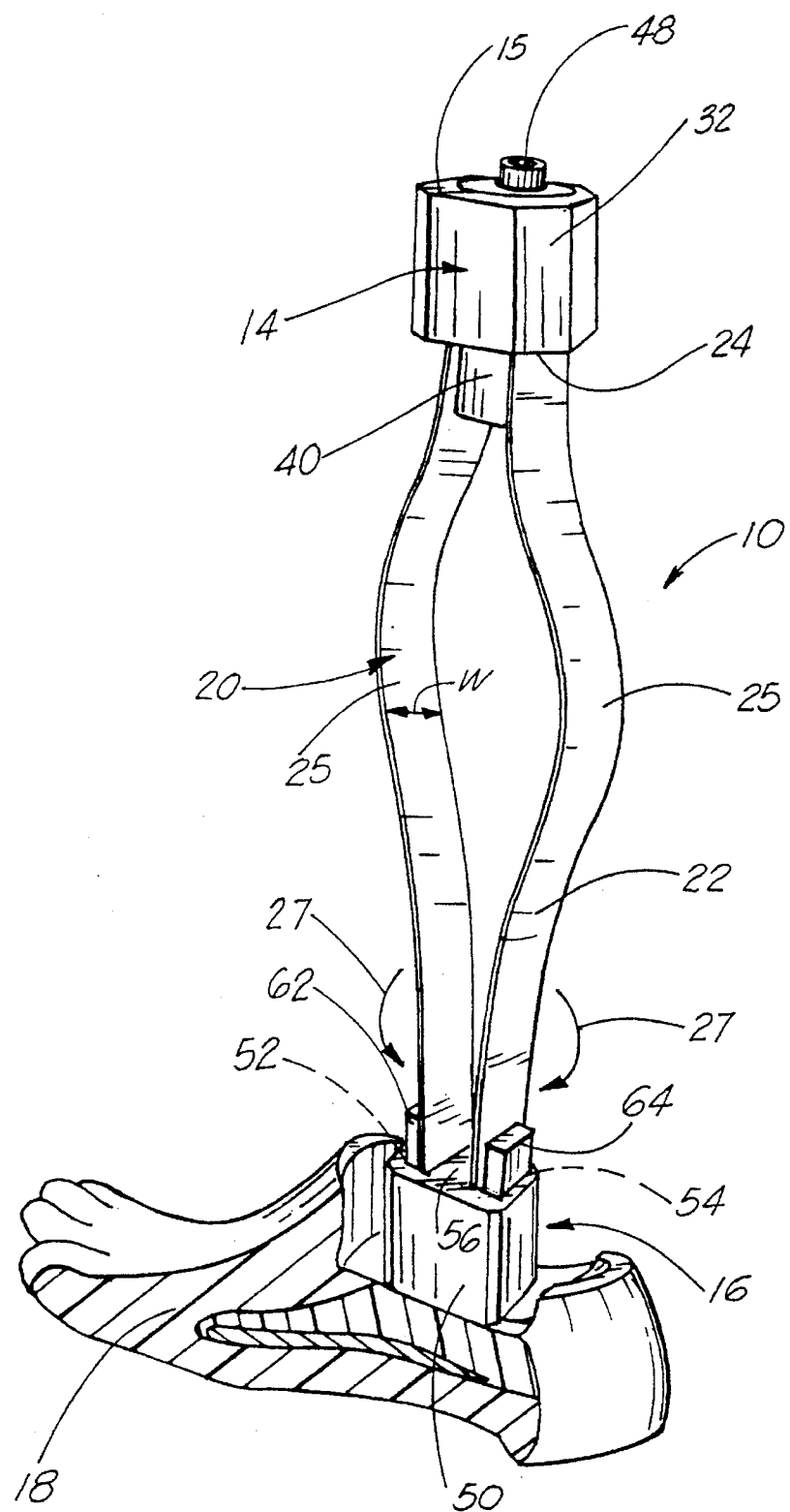
FIG. 1 illustrates an overall partial cutaway view of the preferred embodiment of the prosthetic apparatus of the present invention.

FIGS. 1 through 4 illustrate the preferred embodiment of the improved lower leg strut system of the present invention by the numeral 10. As illustrated in FIG. 1, strut system 10 is a prosthetic device positioned intermediate an upper prosthetic knee 14 and a lower prosthetic ankle 16, which would then be engaged to a lower foot member 18. A second embodiment to be discussed further in FIG. 4 would utilize a socket secured to the upper ends of the prosthetic device 10. As illustrated, strut system 10 comprises a first anterior linear leaf spring member 20, and a second posterior linear leaf spring 22, along substantially the entire length of the lower leg of the wearer, each of the springs 20, 22 having first upper ends 24 and second lower ends 26.

Turning now to the construction of each of the springs 20, 22, reference is made to FIG. 2. As seen, anterior leaf spring 20 is constructed of a lightweight, metal of high strength or laminated fiber. Each of the springs 20, 22 has a principal elongated body member 28 having a width W across its front, and being substantially thin in cross-section along the length, to allow flexion of each of the spring members during use. As is seen in the figures, each of the springs 20, 22, extend substantially in parallel relationship, vertically from their upper ends 24. Substantially midway along each of their lengths, each spring defines a curved or "bowed" portion 25, each of the bowed portions 25, bowing away from one another, as seen in the figures. The curved leaf springs 20, 22, would then resume their parallel relationship as their lower ends 26 are mounted at ankle portion 16, as will be described further. Further, there is illustrated in FIG. 2 achilles tendon 21. Achilles 21 would not necessarily be present in the preferred embodiment of the apparatus as seen in FIG. 1. However, in some embodiments, achilles tendon 21 would be incorporated, which would comprise a flexible belt member 21A extending between an upper mounting ring 21B, mounted to upper knee 14, and a lower mounting ring 21C mounted to lower ankle member 16. In the preferred embodiment of the achilles tendon 21, the ends 21E, 21F of the achilles tendon 21 would be sewn together in stitch line 21D for securing the ends together for forming the continuous loop as illustrated in FIG. 2.

Reference is made to FIG. 2, which illustrates the means of mounting each of the springs 20, 22 to the upper knee portion or prosthetic socket 14 of a prosthetic joint. As is seen, each spring 20, 22 terminates in a blunt upper end 30. There would be provided a prosthetic knee joint 14 comprising body member 32 having a central cavity 34 formed in the underside 36 of prosthetic socket or knee joint 14 for receiving the upper ends 30 of curved springs 20, 22. Cavity 34 would be defined by sidewalls 35. As illustrated, The blunt end 30 of each spring 20, 22 would be received into said cavity 34, the cavity being quite larger than the overall area of the springs 20, 22, and defining a space 38 within the cavity intermediate the two springs 20, 22. There would then be provided a central wedge member 40, having tapered sidewalls 42, 44 and constructed of lightweight metal or the like. Wedge member 40 would then be inserted into the space 38 in the prosthetic knee joint or prosthetic socket 14, and would, upon forcing the wedge member 40 into the space, frictionally engaging against the inner sidewalls of the springs 20, 22, and the sidewalls 35 of the cavity. To provide a permanent engagement between wedge member 40 and the springs 20, 22 within cavity 34, the upper face 41 of wedge 40 would be adapted to receive a threaded member 48, such as a bolt. The bolt 48 would be inserted through a bore 49 in the upper face 15 of prosthetic knee joint body or prosthetic socket 14, and would threadably engage into the threaded bore 49 of wedge 40 to pull wedge 40 in frictional engagement with the upper ends of springs 20, 22 as the bolt 48 is tightened.

Turning now to the engagement of the lower ends 26 of each of the springs 20, 22, into the lower prosthetic ankle 16, reference is again made to FIGS. 1 and 2. As illustrated, there would be provided a prosthetic ankle joint 16, comprising body member 50 having a pair of cavities 52, 54 thereupon for receiving the lower ends 26 of springs 20, 22. Each cavity 52, 54 would be separated by a dividing wall 56, centrally positioned in body 16. As illustrated, The blunt lower end 58 of each spring 20, 22 would be received into each cavity 52, 54 respectively, each cavity being quite larger than the overall area of the springs 20, 22. There would then be provided first and second wedge members 62, 64, constructed of lightweight metal or the like, which would then be inserted into each of the spaces 60 in the prosthetic ankle joint 16, and would, upon forcing the wedges 62, 64 into each space 52, 54, fictionally engage between the springs 20, 22, and the interior walls 53, 55 of each cavity. In a fashion similar to the permanent engagement between the upper ends of springs 20, 22 to the prosthetic knee joint or prosthetic socket 14, the permanent engagement between wedges 62, 64 and the springs 20, 22 within cavities 52, 54, the lower face 63 of each wedge 62, 64 would be adapted to receive a threaded bolt member 51 extending through the lower face 63 of body 16. Each bolt 51 would threadably engage each wedge 62, 64, so that upon tightening of bolts 51, each wedge 62, 64 would be drawn into each cavity to increase their frictional engagement with springs 20, 22, for establishing the permanent binding between the springs 20, 22 and the ankle 16.

In the configuration as described above, the manner in which each of the springs 20, 22 is fictionally engaged at both the knee prosthetic joint or prosthetic socket 14 and the ankle prosthetic joint 16 is critical. In positioning the central wedge 40 into space 37 of the prosthetic knee body or prosthetic socket 14, there is provided a resistance against rotation of the limb at the prosthetic knee joint or prosthetic socket 14. Furthermore, by wedging the curved leaf springs 20, 22 apart at the knee or prosthetic socket section of the prosthesis, a stress or spring rate increases built in to decrease the rotation of horizontal shear moments of these leaf springs at this specific location. Also, by wedging, welding, or bonding the curved linear leaf springs 20, 22, to near parallel at the prosthetic ankle joint 16, allows for a flexion moment of both curved linear leaf springs 20, 22, and the unique ability for these springs to twist or rotate shown by arrows 27 in FIG. 1. This is what is known as horizontal shear.

FIGS. 3A through 3D represent various dynamic movements of the apparatus during the gait movement of a foot during walking. As illustrated in FIG. 3A, there is a prosthetic foot member 18 having the prosthetic strut apparatus 10 mounted onto base plate at ankle joint 16. In this particular embodiment, the apparatus is seen without the use of the achilles tendon member 21, so that a clear view of the movement of the curved leaf springs 20, 22 may be viewed in full view. However, for purposes of the actual combination, there may be included the achilles tendon member 21, as illustrated in FIG. 2, and in the gait movements in FIG. 3-B as will be described further.

Figure 4:
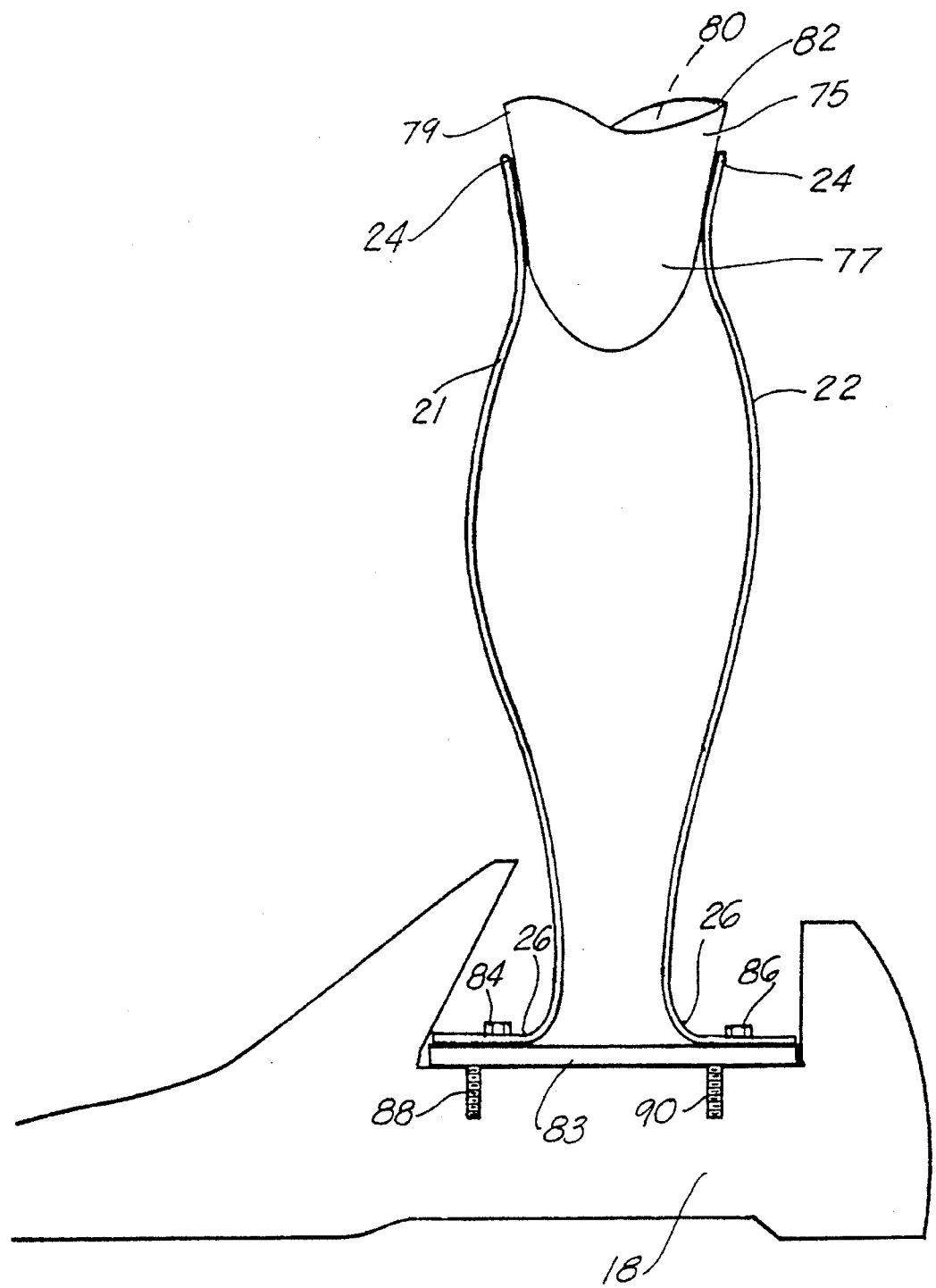
FIG. 4 illustrates an overall side view of the embodiment of the prosthetic apparatus of the present invention utilizing a socket secured to the upper ends of apparatus.

Before discussing the gait movements of FIGS. 3-A through 3-D, reference is made to FIG. 4 which illustrates an embodiment of the present invention utilized with a knee prosthetic socket 75 permanently secured to the upper ends 24 of the leaf springs 21, 22, through laminating or the like. The socket 75 comprises a body member 77, having a continuous surface 79, with an inner hollow 80 having an upper opening 82 thereto for receiving the stump of an amputee. As illustrated, the ends 24 of springs 21, 22 have been spread to accommodate the socket 75. The lower ends 26 of each spring 21, 22 are flared out horizontally, and are boltingly secured to a lower plate 83 via bolts 84, 86. Plate 82 would then be secured to a foot 18 through bolts 88, 90. The description of the movement of the springs 21, 22 as previously discussed, and as will be discussed in relation to FIGS. 3A through 3D, apply to this embodiment as they do to the preferred embodiment as seen in FIGS. 1 and 2.

Turning now to the gait movements, in FIG. 3-A, the foot 18 has moved to mid-stance, so that the ball 19 and toe 17 are lying flat on surface 23, with heel 25 raised off of surface 23 to compensate for normal shoe heel height. In this position the weight of the wearer of the prosthesis is directly on both of the curved leaf spring members 20, 22 (arrow 15), and therefore each of the spring members 20, 22 are non-stressed, and are in the normal non-stressed position as seen in FIGS. 1 and 2.

In FIG. 3-B, the foot 18 is in the position where the toe 17 is striking the surface 23, with the ball 19 and heel 25 of foot 18 moved off of the surface 23. In this position, as illustrated, the anterior leaf spring 20 has compressed anteriorly, in the direction of arrow 33, while the rear leaf spring 22, has elongated inwardly slightly in the direction of arrow 31. Note the presence of the achilles tendon member 21 which would provide for reduced posterior elongation during walking movements.

FIG. 3-C would illustrate the heel 25 striking the surface 23, with the ball 19 of the foot 18 raised off of the surface. In this particular movement of the gait, the posterior leaf spring 22 is being compressed directly outward (arrow 22A), and the anterior leaf spring is substantially non-compressed, and in the normal unstressed position.

In FIG. 3-D, the foot is in the "flat foot" position with the heel 25 and the ball 19 of foot 18 striking the surface 23, with the toe 17 raised off of the surface 23. In this position, which is the opposite of the stressing as undertaken in FIG. 3-B, the anterior leaf spring 20 is elongated inwardly, in the direction of arrow 27, while the posterior leaf spring 22 is flexed rearward, in the direction of arrow 29, as seen in the Figure.

Although not illustrated, the foot 18 may be positioned in the heel off position i.e., with the heel 25 of foot 18, moved off of a surface 23, and the ball 19 of the foot 18, striking the surface 23. In this position, it should be noted that due to the shifting of the weight of the amputee when the foot is placed in this position, the anterior leaf spring member will be compressed anteriorly, and the posterior leaf spring member 22 will be flexed inwardly.

This improved strut assembly 10 is in effect a continuation of the foot ankle system in the multi-axial rotation system as claimed and described in U.S. Pat. Nos. 5,019,109 and 4,718,913. In effect, the system consists of an anterior and posterior component consisting of curved linear leaf springs 20, 22. By curving the linear leaf springs, a flexion (bending) motion is allowed. An achilles band 21, as illustrated in FIG. 2, may also be added to allow both curved linear leaf springs 20, 22 to bend more in unison. Without the achilles band 21, the elongation of the posterior curved linear leaf spring 22 would occur from mid-stance to toe off during the gait cycle as is illustrated in the Figures. These curved linear leaf springs 20, 22 must face each other, i.e. "almond-shaped", in order to function in the correct motion as is illustrated. Different compression strength springs may be applied according to the height, weight and activity level of the amputee. Rotation or horizontal shear is another function of this super strut system which makes this unit unique. There is no telescoping pile on or sliding motion mechanism within this system, and it functions with the least amount of components.

The unique method of securing the curved leaf springs 20, 22 as was described earlier by the unique wedge type clamping mechanism is seen. This frictionally engaged welding, bonding or clamping mechanism allows the curved leaf springs 20, 22 to be positioned differently than any other leaf spring prosthetic unit commercially available. The ability to preload the curved linear leaf springs 20, 22 increases spring function much like the second curve of the Turkish recurve bow did for the archery industry. It is this unique combination of the curvature of the leaf spring coupled with the method of wedgingly attaching the leaf spring to both the prosthetic ankle and the prosthetic knee which allows its versatility and unique qualities.

The following table lists the part numbers and part descriptions as used herein and in the drawings attached hereto.

PARTS LIST

| Part Number | Description |
| --- | --- |
| 10 | strut system |
| 14 | prosthetic knee or prosthetic socket attachment point |
| 15 | upper face |
| 16 | prosthetic ankle |
| 17 | toe |
| 18 | foot member |
| 19 | ball |
| 20 | anterior leaf spring member |
| 21 | achilles tendon member |
| 21A | belt member |
| 21B | upper mounting ring |
| 21C | lower mounting ring |
| 21D | stitch line |
| 21E, 21F | ends |
| 22 | posterior leaf spring member |
| 22A | arrow |
| 23 | surface |
| 24 | upper ends |
| 25 | heel |
| 25 | bowed portion |
| 26 | lower ends |
| 27 | arrows |
| 29 | arrow |
| 30 | blunt upper end |
| 31 | arrow |
| 32 | body member |
| 33 | arrow |
| 34 | central cavity |
| 35 | side walls |
| 36 | underside |
| 40 | central wedge member |
| 41 | upper face |
| 42, 44 | side walls |
| 48 | threaded member (bolt) |
| 49 | bore |
| 50 | body member |
| 51 | |
| 52, 54 | cavities |
| 56 | dividing wall |
| 58 | blunt lower end |
| 62, 64 | first and second wedge members |
| 63 | lower face |
| 65 | threaded bore |
| 70 | threaded member (bolt) |
| 73 | arrow |
| 75 | socket |
| 77 | body |
| 79 | surface |
| 80 | hollow |
| 82 | opening |
| 83 | plate |
| 84, 86 | bolts |
| 88, 90 | bolts |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An improved lower leg prosthesis, comprising:

a) an upper end, having a cavity formed therein, for securing to a prosthetic knee joint or socket;

b) a lower end for securing to a prosthetic ankle joint;

c) a pair of leaf spring members extending between the upper and lower ends of the prosthesis, and secured within the cavity of the upper end of the prosthesis;

d) means associated with each of the leaf spring members for providing flexion of the leaf springs during the walking movements; and e) wedge means positionable in the upper and lower ends of the prosthesis for engaging the upper and lower ends of the leaf spring members within the upper and lower ends of the prosthesis, respectively.

2. The prosthesis in claim 1, wherein each of leaf spring members extend substantially the length of the calf of the prosthesis, and define a bowed central portion along each of their lengths.

3. The prosthesis in claim 1, wherein means positionable in the upper end of the prosthesis further comprises a single wedge insert engaged between the members and threadably engaged to the upper end.

4. The prosthesis in claim 1, wherein the lower end of the prosthesis further comprises at least a pair of cavities, each cavity for receiving a lower end of each of the leaf spring members, with a wedge insert engaged between each spring member within each cavity and each wedge threadably engaged to the lower end.

5. The prosthesis in claim 1, wherein there is further provided an acholous tendon member, further comprising a substantially non-stretchable belt extending from the upper end to the lower end along a rear face of a calf portion of the prosthesis.

6. The prosthesis in claim 3, wherein the securing of the leaf spring with a single wedge in the knee portion defines a region of reduced rotatability between the knee joint and the prosthesis.

7. The prosthesis in claim 4, wherein the securing of the leaf springs with the pair of wedge inserts in the ankle joint defines a region of increased rotatability between the ankle joint and the prosthesis.

8. The prosthesis in claim 1, wherein the upper ends of the leaf springs may be attached to a socket for accommodating a stump, or a knee joint.

9. An improved lower leg prosthesis, comprising:

a) an upper end for securing to a prosthetic knee joint or socket, and further comprising a cavity therein;

b) a lower end for securing to a prosthetic ankle joint, said lower end further comprising a pair of cavities therein;

c) a pair of leaf spring members extending between and secured within the cavity of the upper end and the pair of cavities in the lower end of the prosthesis, each of leaf spring members extending substantially the length of the prosthesis, and defining a bowed central portion along each of their lengths, for providing flexion of the leaf springs during the walking movements; and d) wedge inserts positionable in the cavities of the upper and lower ends of the prosthesis for frictionally engaging the upper and lower ends of the leaf spring members within the respective ends of the prosthesis.

10. The prosthesis in claim 9, wherein there is further provided an acholous tendon member, further comprising a substantially non-stretchable belt extending from the upper end to the lower end along a rear face of a calf portion of the prosthesis.

11. The prosthesis in claim 9, wherein the securing of the leaf spring with a single wedge in the knee joint defines a region of reduced rotatability between the knee joint and the prosthesis.

12. The prosthesis in claim 9, wherein the securing of the linear springs with the pair of wedge inserts in the ankle joint defines a region of increased rotatability between the ankle joint and the prosthesis.

13. The prosthesis in claim 9, wherein the bowed regions of the leaf spring members further define a means for preloading the leaf spring members to increase the spring function of the leaf spring members during walking movements.

14. In a prosthetic limb, of the type having a lower prosthetic ankle portion, an upper prosthetic knee portion, and a calf portion intermediate the ankle and knee portions, the improvement comprising:

a) a pair of leaf spring members, each of the members including a bowed region along their length, and further comprising wedge means for frictionally engaging ends of the leaf spring members within cavities formed in each of the knee and ankle portions; and b) an Achilles tendon strap engaged between the upper knee joint and the lower ankle joint, said strap being of substantially non-stretchable material for allowing reduced flexion of at least one of the leaf springs during certain walking movements.

15. In a prosthetic limb, of the type having a lower prosthetic ankle portion, an upper prosthetic knee portion, and a calf portion intermediate the ankle and knee portions, the improvement comprising:

a. a pair of leaf spring members, each of the members having an upper and lower end, and including a bowed region along their length;

b. a first single wedge insert engaged between the upper ends of the leaf spring members within a cavity formed in the knee portion for engaging the upper ends of the leaf spring members and at least a pair of wedge inserts engaging the lower ends of the leaf spring members within the cavity formed in the ankle portion of the prosthesis; and c. socket means in the knee portion secured to the upper ends of the spring members, for accommodating the stump of an amputee.

* * * * *